United States Patent [19]

Baldwin et al.

[11] 4,360,511
[45] Nov. 23, 1982

[54] AMINES USEFUL AS BRAIN IMAGING AGENTS

[75] Inventors: Ronald M. Baldwin, San Francisco; Tz-Hong Lin, Fremont; Harry S. Winchell, Lafayette, all of Calif.

[73] Assignee: Medi-Physics, Inc., Emeryville, Calif.

[21] Appl. No.: 161,097

[22] Filed: Jun. 19, 1980

Related U.S. Application Data

[63] Continuation of Ser. No. 964,561, Nov. 29, 1978, abandoned.

[51] Int. Cl.³ .................. A61K 49/00; A61K 43/00
[52] U.S. Cl. .................. 424/1.5; 564/373; 564/374; 564/384
[58] Field of Search .................. 564/373, 374, 384; 424/1, 9, 1.5

[56] References Cited

U.S. PATENT DOCUMENTS

| | | | |
|---|---|---|---|
| 4,021,224 | 5/1977 | Pallos et al. | 260/558 A |
| 4,048,297 | 9/1977 | Counsell et al. | 424/1 |
| 4,053,509 | 10/1977 | Faro et al. | 260/557 B |
| 4,104,383 | 8/1978 | Krausz | 260/570.5 R |

OTHER PUBLICATIONS

Blaschke et al., *Chem. Ber.*, 108:2792 (1975).

*Primary Examiner*—Christine M. Nucker
*Attorney, Agent, or Firm*—Jon S. Saxe; George M. Gould; William H. Epstein

[57] ABSTRACT

Certain radioiodine containing amines useful as brain imaging agents are disclosed. The compounds of the invention are represented by the formula

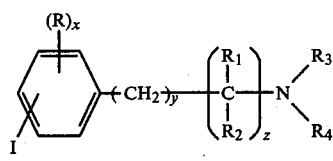

wherein I is a radioisotope of iodine with I-123 being preferred, R is lower alkyl or halogen, $R_1$ and $R_2$ are the same or different and are selected from the group consisting of hydrogen and lower alkyl, $R_3$ and $R_4$ are the same or different and are selected from the group consisting of hydrogen, alkyl, aryl, substituted aryl, aralkyl, substituted aralkyl and substituted carbamoyl methyl or $R_3$ and $R_4$ taken together with the nitrogen to which they are attached form a 5- or 6-membered ring which may be substituted with one or more lower alkyl groups, x is 0 to 4, y is 0 to 3 and z is 0 or 1 and pharmaceutically acceptable acid addition salts thereof.

14 Claims, No Drawings

AMINES USEFUL AS BRAIN IMAGING AGENTS

This is a continuation, of application Ser. No. 964,561 filed Nov. 29, 1978, abandoned.

STATEMENT OF PRIOR ART

The use of radioiodine to label organic compounds for use in diagnostic nuclear medicine is well documented in the literature. Radioiodinated human serum albumin, fatty acids and triglycerides as well as orthoiodohippuric acid have long been available for such diagnostic purposes. The preparation of I-131-labeled iodobenzoic acids for liver function procedures is described by Tubis et al., Int. J. Applied Radioisotopes 15, p. 397 (1964). The use of p-iodobenzoyl chloride (I-131) to label antibodies for the determination of in vivo protein distribution is reported by Blau et al., Int. J. Appl. Radiat. Isot. 3, pp 217–225 (1958).

The use of the N-hydroxysuccinimide ester of 3-(4-hydroxyphenyl) propionic acid-I-125 to label proteins is reported by Bolton and Hunter, Biochem J 133, pp 529–539 (1973). Smith, U.S. Pat. No. 3,979,506 describes imidoesters of radionuclide-substituted hydroxy or alkoxy phenyls wherein the radionuclide can be, for example, I-125.

The art has been apprised that certain radiolabeled compounds will localize in the brain to a level such to allow for imaging thereof. Recently there has been increasing interest in finding compounds which will more effectively cross the blood-brain barrier thus facilitating more efficacious imaging of the brain.

Friedman et al, in a paper presented at the Second International Symposium on Radiopharmaceutical Chemistry at St. Catherine's College, Oxford, in July 1978 described the preparation of Br-76 and Br-77 labeled L-Dopa and 5-hydroxytryptophan. These compounds were shown to be decarboxylated in vivo and carried some activity across the blood/brain barrier.

Winstead et al., J Nucl Med 16 #11, pp 1049–1057 (1975), described studies in animals indicating brain uptake of certain labeled aminonitriles. The clinical efficacy of these compounds, however, has not been established. Robinson et al, J Nucl Med 17, p 1093 (1976) described I-123 labeled 4-iodoantipyrine as a brain-imaging agent. The rapid in vivo deiodination and suboptimal concentration in the brain of this compound limit its utility.

Braun et al., J Med Chem 20 #12, pp 1543–1546 and Sargent III et al., J Nucl Med 19 #1, pp 71–76 (1978) describe the synthesis and brain uptake of I-123 labeled 4-iodo-2,5-dimethoxyphenylisopropylamine. The authors describe the potential of this compound in the imaging of the normal brain as well as possessing possible application in the study of mental disorders. The authors emphasize the criticality of the positioning of the iodo substituent on the ring in relation to the two methoxy groups.

The compounds of the subject invention are chemically distinct from those reported in the literature and they facilitate the rapid passage of a radioisotope of iodine, preferably I-123, across the blood/brain barrier. I-123 is preferred because it compares very favorably with I-131 in terms of half-life and absorbed radiation dose.

Because the half-life of I-123 is only 13 hours, however, it is necessary that the procedures utilized to label organic compounds therewith be both rapid and efficient. Further, it is necessary, as with any radiolabeled compound, that the radiolabel (in the case of radioiodinated compounds, the iodine-to-carbon bond) be stable in vivo with minimal loss of radionuclide from the labeled compound after its administration to the patient. The compounds provided in accordance with the present invention satisfy all of these requirements.

The radioiodinated compounds of the present invention are novel compounds. Certain aminoalkyliodobenzenes and aminoiodobenzenes wherein the iodine is not a radioisotope are known. For example, Ruchdeschel et al., Pharmazie 31, pp 374–381 (1976) disclose among a number of compounds tested for tuberculostatic effect, N-butyl-3-iodobenzylamine. Dimroth et al., Naturwissenschaften 46, p 557 (1959) disclose, among other compounds, p-iodo-N,N-dimethyl- and p-iodo-N,N-diethylaniline. No indication of utility is given.

U.S. Pat. No. 3,726,969 issued Apr. 10, 1973 discloses a method of accelerating the lysis of blood clots with urokinase and a benzylamine derivative which includes, among others, p-iodo-benzylamine. Remy et al., J Med Chem 18, pp 142–148 disclose a series of antiarrhythmic agents which include meta- and para-iodo-N,N-dimethylbenzylamine. Ecsery et al., Austrian Pat. No. 271,436 published June 10, 1969 disclose among a series of psychostimulants 1-(p-iodophenyl)-2-(methylamino)-propane.

The disclosures of the foregoing compounds do not suggest the use of the novel radioiodinated compounds of the subject invention as brain scanning agents.

DETAILED DESCRIPTION OF THE INVENTION

The present invention is directed to radioiodinated amines represented by the formula

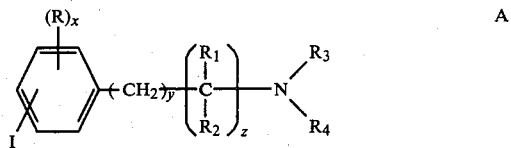

wherein I is a radioisotope of iodine with I-123 being preferred, R is lower alkyl or halogen, $R_1$ and $R_2$ are the same or different and are selected from the group consisting of hydrogen and lower alkyl, $R_3$ and $R_4$ are the same or different, and are selected from the group consisting of hydrogen, alkyl, aryl, substituted aryl, aralkyl, substituted aralkyl or $R_3$ and $R_4$ taken together with the nitrogen to which they are attached form a 5- or 6-membered ring which may be substituted with one or more lower alkyl groups, x is 0 to 4, y is 0 to 3 and z is 0 or 1, and pharmaceutically acceptable acid addition salts thereof.

The compounds of formula A are useful for imaging of the brain. As will therefore be appreciated, the compounds of formula A demonstrate rapid accumulation in the brain indicative of an ability to penetrate the so-termed "blood/brain barrier."

In comparison to I-123 labeled 4-iodoantipyrine mentioned above, the compounds of formula A demonstrate a marked superiority in stability of the iodine-carbon bond in vivo. The stability of the carbon-iodine bond in vivo in combination with the ability to penetrate the blood/brain barrier enable the compounds of formula A to demonstrate rapid localization of the radioiodine in the brain following intravenous administration. In addition to the primary localization in the brain, the compounds of formula A also show localization in the heart, adrenals and pancreas.

The stability of the iodine label in vivo; i.e., in the brain, and the ability to penetrate the blood/brain barrier are distinct advantages of the compounds of formula A in their use as brain imaging agents.

As utilized herein, the term "alkyl" indicates a straight- or branched-chain radical containing from 1 to 18 carbon atoms such as, for example, methyl, n-propyl, isopropyl, tertiary butyl, n-hexyl, n-octadecyl and the like.

The term "lower alkyl" denotes a straight- or branched-chain alkyl radical having from 1 to 6 carbon atoms. The term "aryl" as utilized herein means an aromatic, mononuclear or polynuclear hydrocarbon such as, for example, phenyl, naphthyl and phenanthryl, with phenyl being preferred. The alkyl portion of "aralkyl" as utilized herein is a straight- or branched-chain alkyl having from 1 to 6 carbon atoms. Preferred aralkyl radicals are benzyl, phenylisopropyl and phenethyl.

The terminology "substituted aryl" and "substituted aralkyl" as utilized herein indicate an aryl radical or an aralkyl- or branched-chain radical having 1 to 6 carbon atoms, an alkoxy radical, the alkyl portion of which is as just defined, hydroxy or halogen. Preferred among this group is orthoiodobenzyl. The term "halogen" as utilized herein indicates fluoro, chloro, bromo, iodo or trifluoromethyl. The terminology "substituted carbamoylmethyl" as utilized herein indicates a carbamoylmethyl radical having substitution on either the nitrogen or the methylene bridge. Said substituents are preferably aryl or substituted aryl.

In formula A, where x is greater than 0, it is preferred that x equals 1. Wherein $R_3$ and $R_4$ together with the nitrogen to which they are attached form a 5- or 6-membered heterocyclic ring, such rings may include an additional hereto atom selected from the group consisting of oxygen, nitrogen and sulfur. Examples of preferred groups in accordance with the invention are pyrolidino, pyridino, piperidino, morpholino and thiomorpholino with piperidino being preferred. In formula A, I can be ortho, meta or para to the amine group with para being preferred.

As stated above "I" indicates all radioisotopes of iodine; e.g., I-123, I-125 and I-131. Of these, I-123 is particularly preferred in the practice of the invention.

The pharmaceutically acceptable acid additional salts of the compounds of formula A include salts with both inorganic and organic pharmaceutically acceptable acids. Suitable inorganic acids include, for example, hydrochloric acid, hydrobromic acid, hydriodic acid, sulfuric acid and the like. Suitable organic acids include, for example, benzoic acid, acetic acid, citric acid, lactic acid and the like.

Preferred radioiodinated amines in accordance with the present invention include:
I-123-p-iodo-α-methylbenzylamine;
I-123-N-isopropyl-p-iodo-α-methylbenzylamine;
I-123-R-p-iodoamphetamine;
I-123-S-p-iodoamphetamine;
I-123-R-N-isopropyl-p-iodoamphetamine;
I-123-S-N-isopropyl-p-iodoamphetamine;
I-123-N-isopropyl-o-iodobenzylamine; and
I-123-N-t-butyl-o-iodobenzylamine.

The compounds of formula A can be prepared by methods recognized in the art. For example, a compound of formula A may be prepared by reacting a compound represented by the formula.

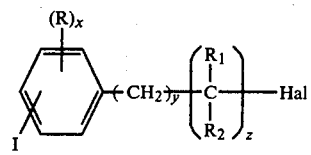

B wherein I, x, R, $R_1$ and $R_2$ are as previously defined, y is 1 and z is 0 and Hal is chloro, bromo or iodo With an amine represented by the formula

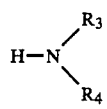

C wherein $R_3$ and $R_4$ are as previously defined.

For the above reaction, the amine may be utilized to create alkaline conditions, i.e. added in excess, or the reactants may be present in stoichiometric quantities and the reaction carried out in the presence of a suitable base such as, for example, sodium hydroxide, potassium hydroxide and the like. The reaction is carried out at ambient temperature or with heating, e.g. at a temperature up to about 200° C., preferably at about 25° C.

Certain compounds of formula A are prepared by reacting a compound of formula A wherein at least one of $R_3$ and $R_4$ is hydrogen with a compound represented by the formula

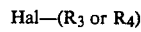

D wherein Hal is chloro, iodo or bromo and $R_3$ and $R_4$ are as defined above with the exception that they are not aryl.

The reaction with the compound of formula D is preferably conducted under the same general conditions as for the reaction of compounds of formulae B and C. Generally, the amine can be used as a solvent for the reaction if it is a liquid. The reactants can also be dissolved in a suitable inert organic solvent such as, for example, ethyl ether, methanol, ethyl acetate, dioxane, methylene chloride, benzene, N,N-dimethylformamide, tetrahydrofuran and the like with ethyl ether and methanol being preferred. The amine compounds of formulae A and C may also be reacted in the form of their acid additional salts utilizing an appropriate base to generate the free amine in situ.

Certain compounds of formula A may also be prepared by reacting a compound of formula A wherein at least one of $R_3$ and $R_4$ is hydrogen with an aldehyde or ketone represented by the formula

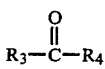

E wherein $R_3$ and $R_4$ are as defined above to form the corresponding Schiff base and then reducing the Schiff base chemically or catalytically.

Compounds of formula A wherein $R_3$ and $R_4$ together with the nitrogen to which they are attached form a 5- or 6-membered ring may be prepared by reacting a compound of formula A wherein $R_3$ and $R_4$ are hydrogen with a compound represented by the formula $$\begin{array}{c} CHO \\ | \\ (CH_2)_n \\ | \\ CHO \end{array} \qquad F$$

wherein n is 2 or 3.

The reduction of the Schiff base as described above may be carried out either chemically or catalytically by methods well known in the art. A preferred chemical method for reduction of the Schiff base utilizes an alkali metal cyanoborohydride as the reducing agent in a suitable organic solvent such as, for example, methanol, dioxane and tetrahydrofuran, with methanol being preferred.

Compounds of formula A wherein z is 0, y is 1 to 3 and $R_3$ and $R_4$ are each hydrogen may be prepared by the reduction, preferably chemically, of a compound represented by the formula

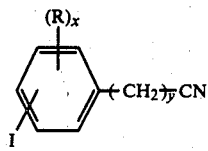 G wherein R and x are as defined above and y is 0 to 2. The chemical reduction is preferably carried out using a boron hydride such as, for example, borane-tetrahydrofuran or an alkali metal aluminum hydride such as lithium aluminum hydride or the like at a temperature of from about 0° C. to about 100° C., preferably 25° C. in an organic solvent such as ethyl ether, tetrahydrofuran and 1,2-dimethoxymethane, with tetrahydrofuran being preferred.

Finally, compounds of formula A wherein I is para may be prepared by the iodination of an amine having the amine group protected, e.g. by an alkanoyl group, i.e. a compound represented by the formula

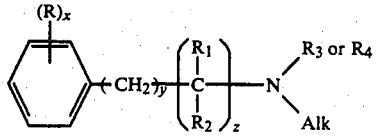 H wherein R, $R_1$, $R_2$, $R_3$, $R_4$, x, y and z are as defined above except that no R is in the para position and Alk is an alkanoyl group, and subsequently removing the protecting alkanoyl group by conventional methods. The iodination is carried out by conventional methods such as utilizing iodine in the presence of an oxidizing agent such as iodic acid or nitric acid at elevated temperatures. The alkanoyl protecting group can be removed, for example, by hydrolyzing in acid medium under reflux.

The above reactions can be carried out utilizing the respective compounds wherein I is stable iodine and not a radioisotope of iodine under the same conditions. The resulting compounds wherein I is stable iodine; i.e. the cold compounds, are than exchange labeled with a radioisotope of iodine, preferably I-123.

For the exchange radiolabeling process, an inorganic salt of a radioisotope of iodine, preferably an alkali metal salt and most preferably the sodium salt is utilized. The salt is heated with the cold compound of formula A; i.e. a compound of formula A wherein I is stable iodine and not a radioisotope of iodine for from about ¼ to about 2 hours. The exchange radiolabeling is carried out in the presence of an inert organic solvent such as, for example, a lower alcohol or those named above.

The radiolabeled compound of formula A is then dissolved in a suitable solvent; e.g. ethyl ether, and washed with aqueous sodium bisulfite solution to remove unexchanged radioiodine. The product is then extracted into hydrochloric acid and washed with a suitable water immiscible organic solvent; e.g. ethyl ether, then basified with a suitable aqueous base and re-extracted into the organic solvent. The organic solution is then evaporated to dryness to obtain a pure labeled product.

The radiolabeling procedure described above may likewise be carried out starting with an acid addition salt of a compound of formula A by treating it with a suitable base and then extracting the free amine with a suitable organic solvent such as those named above.

Intermediate compounds such as, for example, those of formula B above can be radiolabeled in a like manner and then reacted as discussed above to form the corresponding compound of formula A. Many of the cold compounds of formulae A through H are known compounds.

In addition to the partition procedure described above, the radiolabeled compounds of formula A and the intermediates can be purified by preparative thin layer chromatography and liquid chromatography utilizing procedures well known in the art.

The compounds of formula A can be rapidly prepared, e.g. by exchange radiolabeling. This is advantageous because of the criticality of time in the handling of radioisotopes which have a comparatively short half life such as iodine I-123.

The compounds of formula A as well as the corresponding cold compounds can be converted to their respective pharmaceutically acceptable acid addition salts by methods conventional the art, for example, by direct reaction with the appropriate acid. The hydrochloride can be prepared, for example, by contacting a solution of the amine of formula A in a suitable organic solvent with hydrogen chloride gas and recovering the precipitated amine hydrochloride.

As stated above, the radioiodine containing compounds of the invention rapidly localize in the brain following intravenous administration. In most instances, a sufficient amount of the administered dose will accumulate in the brain within from about one to ten minutes to permit the taking of scintiphotos. The compounds of the invention will show meaningful presence in the brain for at least 15 minutes so that significant studies may be carried out. In addition to the brain, the compounds of formula A will also accumulate in myocardium, adrenals and pancreas to varying degrees.

The radioiodinated compounds of the subject invention may be administered in an aqueous or aqueous/alcoholic medium. Such media may also contain conventional pharmaceutical adjunct materials such as, for example, pharmaceutically acceptable salts to adjust the osmotic pressure, buffers, preservatives and the like.

A preferred vehicle for the parenteral administration of the compounds of formula A is normal saline which would contain from about 0.5% by weight to about 2% by weight of a suitable preservative.

The following examples further illustrate the invention. Unless otherwise noted, all temperatures are in degrees centigrade.

EXAMPLE 1 o-Iodobenzyl bromide was prepared by the procedure described by H. A. Sloviter, J. Am. Chem. Soc. 71, p.3360 (1949) for p-iodobenzyl bromide by starting with o-iodotoluene. The crude product was distilled at reduced pressure to yield a liquid product, bp. 85°–92°/0.5 mm Hg, which crystallized spontaneously to yield a solid product having a mp of 42°–49°.

o-Iodobenzyl chloride was prepared from o-iodobenzyl alcohol using thionyl chloride according to the procedure described by Brooks et al, Org. Syn. Coll. Vol. 3, p. 698 (1955). The crude product was distilled at reduced pressure to yield a clear, colorless liquid having a bp of 143°/4 mm Hg.

m-Iodobenzyl chloride was prepared in a like manner. Distillation of the crude product gave a 77% yield of colorless liquid, bp 116°–117°/1 mm Hg.

EXAMPLE 2

A total of 1.74 g of o-iodobenzyl bromide prepared in example 1 was stirred with 10 ml of t-butylamine for 18 hrs. at 25°. The resulting fine white precipitate was collected by suction filtration and washed with 10 ml ether to yield 646 mg of t-butylamine hydrobromide. The filtrate was concentrated on a rotary evaporator to a viscous liquid which was dissolved in 25 ml ether and washed with three 20 ml portions of water and two 10 ml portions of 1 N hydrochloric acid.

The combined acidic washings were basified with 5 ml 5 N sodium hydroxide and extracted with 25 ml of ether. The ether solution was washed with four 10 ml portions of water, until the pH of the washing was less than 9, followed by 20 ml saturated sodium chloride solution. The ether solution was then dried with anhydrous magnesium sulfate, filtered and the solvent removed on a rotary evaporator to yield 1.36 g of colorless liquid which was purified by molecular distillation at 80°/0.25 mm to yield 1.11 g of N-t-butyl-o-iodobenzylamine, $R_f$ value of 0.31 on thin layer chromatography on silica gel 60 (1% $CH_3OH/CHCl_3$).

EXAMPLE 3

In accordance with the procedure of example 2 N-isopropyl-o-iodobenzylamine, $R_f=0.57$, was prepared from o-iodobenzyl chloride and isopropylamine.

In a like manner m-iodobenzyl chloride and isopropylamine were reacted to yield N-isopropyl-m-iodobenzylamine, $R_f=0.36$, o-iodobenzyl bromide and di-isopropylamine were reacted to yield N,N-diisopropyl-o-iodobenzylamine, $R_f=0.52$, o-iodobenzyl bromide and piperidine were reacted to yield N-o-iodobenzylpiperidine, $R_f=0.40$, and o-iodobenzyl bromide and 2,6-dimethylpiperidine were reacted to yield N-o-iodobenzyl-2,6-dimethylpiperidine, $R_f=0.55$.

EXAMPLE 4

A total of 3.71 g of o-iodobenzyl chloride prepared in example 1, 1.50 ml aniline and 1.65 ml of 10 N sodium hydroxide in 10 ml of methanol were stirred vigorously for 1.5 days at 25°. Most of the solvent was removed on a rotary evaporator and the residue was treated with 20 ml of ether. The reaction mixture was washed with two 20 ml portions of water and extracted with 30 ml of 2 N hydrochloric acid. The acid solution was washed with 20 ml of ether, rendered alkaline with 10 ml of 10 N sodium hydroxide and extracted with two 20 ml portions of ether. The ether extracts were combined and washed with three 15 ml portions of water until neutral, then with 20 ml saturated NaCl solution and dried over anhydrous magnesium sulfate. Removal of the solvent on a rotary evaporator yielded 680 mg of a light brown liquid.

The product was purified by column chromatography utilizing 20 g silica gel 60-F, eluting with chloroform to give 81 mg of a light tan solid which was recrystallized from petroleum ether to yield 38 mg of white crystals of N-o-iodobenzylaniline. Thin layer chromatography with 50% methanol/hexane showed an $R_f$ value of 0.61. Gas liquid partition chromatography retention time of the product on 3% SE-30* (10'×1/8", 20 ml/min.) at 120° was 9.6 min.

*A methyl silicone polymer manufactured by General Electric Company.

EXAMPLE 5

In accordance with the procedure of example 4 p-iodoaniline and α-bromophenylacetamide were reacted to yield α-(p-iodoanilino)phenylacetamide, $R_f=0.65$.

In a like manner p-iodoaniline and benzyl chloride were reacted to yield N,N-dibenzyl-p-iodoaniline, $R_f=0.71$, ethylamine and o-iodo-benzyl chloride were reacted to yield N-ethyl-o-iodobenzylamine, $R_f=0.55$, propylamine and o-iodo-benzyl chloride were reacted to yield N-propyl-o-iodobenzylamine, $R_f=0.67$, p-iodoaniline and phenethyl bromide were reacted to yield N-β-phenethyl-p-iodoaniline, $R_f=0.73$, β-phenethylamine and o-iodobenzyl bromide were reacted to yield N-β-phenethyl-o-iodobenzylamine, $R_f=0.64$, N-β-phenethyl-o-iodo-benzylamine and phenethyl bromide were reacted to yield N,N-di-β-phenethyl-o-iodobenzylamine, $R_f=0.64$, ethylamine and o-iodobenzyl chloride were reacted to yield N,N-di-o-iodobenzylethylamine, $R_f=0.80$, 2,5-dimethylpyrrolidine and o-iodobenzyl chloride were reacted to yield N-o-iodobenzyl-2,5-dimethylpyrrolidine, $R_f=0.78$, and N-isopropyl-β-phenethylamine and o-iodo-benzyl bromide were reacted to yield N-β-phenethyl-o-iodo-β-phenethylamine, $R_f=0.66$.

EXAMPLE 6

In accordance with the procedure of example 4, o-iodophenethylamine as the hydrochloride was reacted with methyl iodide to form N-methyl-o-iodo-β-phenethylamine. An equivalent amount of sodium hydroxide was added to generate the free amine in situ.

N-β-phenethyl-o-iodo-β-phenethylamine and N-(2,6-dimethylphenylcarbamoyl) methyl-o-iodo-phenethylamine were prepared in a like manner using phenethyl bromide and N-2,6-dimethylphenyl-α-bromoacetamide, respectively, as the starting halides.

EXAMPLE 7

To a solution of 0.71 g of o-iodophenethylamine hydrochloride and 0.145 g acetone in 5 ml of methanol was added an equimolar amount, i.e. 0.139 g of $NaBH_3CN$. The mixture was stirred at room temperature for three days. The mixture was then adjusted to pH 1 with 2 N hydrochloric acid and the methanol removed by purging the mixture with nitrogen. The residue was extracted with 15 ml of chloroform. The extract was diluted with 100 ml of ether and the precipitated amine hydrochloride collected by filtration.

Recrystallization of the product from methanol/ether yielded 0.244 g of N-isopropyl-o-iodophenethylamine, as a white crystalline solid, mp 159°–160°, $R_f$ value=0.28.

EXAMPLE 8

In accordance with the procedure of example 7 the following compounds were prepared:

N-benzyl-o-iodoaniline, $R_f$=0.45, by reacting o-iodoaniline and benzaldehyde;

N-$\beta$-phenethyl-o-iodoaniline, $R_f$=0.31, by reacting o-iodoaniline and phenylacetaldehyde;

N-isopropyl-o-iodoaniline, $R_f$=0.50, by reacting o-iodoaniline and acetone;

N-(o-iodophenyl)amphetamine (dl), $R_f$=0.86, by reacting o-iodoaniline and phenylacetone;

N-isopropyl-p-iodoaniline, $R_f$=0.57, by reacting p-iodoaniline and acetone,

N-o-iodobenzylamphetamine (dl), $R_f$=0.70, by reacting dl-amphetamine and o-iodobenzaldehyde;

N-propyl-o-iodo-$\beta$-phenethylamine, $R_f$=0.46, by reacting o-iodo-phenethylamine and propionaldehyde;

N-o-iodo-$\beta$-phenethylamphetamine (dl), $R_f$=0.46, by reacting o-iodo-phenethylamine and phenylacetone;

N-o-iodo-$\beta$-phenethylpiperidine, $R_f$=0.54, by reacting o-iodo-phenethylamine and glutaraldehyde;

N,N-di-$\beta$-phenethyl-o-iodo-$\beta$-phenethylamine, $R_f$0.47, by reacting N-$\beta$-phenethyl-o-iodo-$\beta$-phenethylamine and phenylacetaldehyde;

R-N-isopropyl-p-iodoamphetamine, $R_f$=0.44, by reacting R-p-iodoamphetamine and acetone and S-N-isopropyl-p-iodoamphetamine, $R_f$=0.46, by reacting S-p-iodoamphetamine and acetone.

EXAMPLE 9

2.19 Grams of p-iodoaniline and 1.06 g of benzaldehyde were dissolved in 50 ml of glyme and the resulting solution heated to 60° for two hours. The temperature was maintained for an additional hour after the addition of 30 ml of a 1 M solution of borane in tetrahydrofuran. The excess boron hydride was then destroyed by the addition of about 10 ml of methanol. To this mixture was added 100 ml of a 0.3 M solution of sodium hydroxide and the resulting solution extracted with 100 ml of ether to yield N-benzyl-p-iodoaniline, $R_f$=0.70.

EXAMPLE 10

Thirty grams of o-iodophenylacetonitrile was added to 230 ml of a 0.6 M solution of borane in tetrahydrofuran and the mixture stirred at room temperature for one hour. The mixture was then heated to boiling until the volume was reduced to about 50 ml. The excess boron hydride was destroyed by the addition of about 10 ml of methanol. Concentrated hydrochloric acid, 15 ml, was added to decompose the complex and the resulting slurry was extracted with two 150 ml portions of ether. Crude product obtained by filtration was purified by dissolving in methanol and precipitation with ether. There was thus obtained o-iodophenethylamine hydrochloride, $R_f$=0.2.

EXAMPLE 11

Ammonia gas was bubbled into a solution of 0.464 g of o-iodobenzaldehyde in 5 ml of ethanol. The excess ammonia gas was removed by nitrogen purging and a solution of 0.1 g sodium cyanide in 0.6 ml of deionized water and 0.12 ml of glacial acetic acid were added with gentle heating for ten minutes. Distilled water was then added until the reaction mixture turned cloudy. Refrigeration subsequently yielded 0.59 g of oily $\alpha$-amino-o-iodophenylacetonitrile, $R_f$=0.7.

EXAMPLE 12

$\alpha$-Bromophenylacetic acid, 8.6 g, was combined with 40 ml of thionyl chloride and heated to a temperature of 70° for one hour. The resulting mixture was treated with 60 ml of benzene and boiled to a volume of 50 ml. Concentrated ammonium hydroxide was then added until the mixture was basic to litmus paper. The residue was taken up into 100 ml ether which was washed several times with 0.1 N sodium hydroxide and deionized water. Evaporation of the ether and purification yielded $\alpha$-p-iodoanilinophenylacetamide, mp 134°–137°.

EXAMPLE 13

A mixture of 7.5 g R-N-acetylamphetamine, 15 ml glacial acetic acid, 5 ml deionized water, 5 g iodine, 2.5 g iodic acid, 2.5 ml concentrated sulfuric acid and 2.5 ml carbon tetrachloride was heated under reflux for 17 hours. The mixture was cooled and diluted with 50 ml deionized water and 15 ml chloroform. The mixture was washed three times with basic sodium bicarbonate and then with deionized water until the washing solution was neutral to litmus paper. The chloroform was evaporated and the residue hydrolyzed by refluxing in 100 ml of 6 N hydrochloric acid for 14 hours. The reaction mixture was cooled and the resulting crystals collected by suction filtration. The crystals were washed with hot chloroform and rendered basic with 50 ml of 4.5 N sodium hydroxide. The product was extracted with 100 ml of ether which, upon evaporation, yielded 4.2 g of R-p-iodo-amphetamine, $R_f$=0.3.

By the same procedure, S-p-iodo-amphetamine was prepared, $R_f$=0.3.

EXAMPLE 14

1.56 Grams of N-isopropyl-m-iodobenzylamine prepared in example 3 was dissolved in 50 ml of ether and cooled in ice. The mixture was briefly purged with nitrogen, and hydrogen chloride gas was introduced into the mixture with rapid stirring until saturation occurred, about 2 minutes. The mixture was again purged with nitrogen, and the white precipitate was collected by filtration, washed with three 10 ml portions of ether and dried for 30 minutes at 25°/1 mm. The hydrochloride salt was recrystallized from 20 ml of chloroform containing 1 ml methanol. TLC of the product in the same mixture showed an $R_f$ of 0.36.

EXAMPLE 15

In a clean pyrex test tube was placed 10 mcl of N-t-butyl-o-iodobenzylamine prepared in example 2 and 4.08 mCi I-123-NaI in acetone. The solvent was evaporated with a stream of nitrogen, 40 ml of ethanol was added and the tube sealed with a torch.

The tube was heated in an autoclave at 121° for one hour. The tube was opened and the mixture taken up in 2 ml of ether. The ether solution was washed with a mixture of 1 ml 0.1 M potassium iodide, 1 ml 1% sodium bisulfite and 0.1 ml 1 N sodium hydroxide, followed by 1 ml water and was extracted with 1 ml 1 N hydrochloric acid. The resulting solution was washed with 1 ml ether, rendered alkaline with 1.2 ml 1 N sodium hydroxide and extracted with 1 ml ether. The ether solution was washed with two 1 ml portions of water. The ether solution was found to contain 85% of the original activity. A control tube containing no substrate but otherwise treated in the same manner showed less than 1% of the original activity in the ether solution.

The ether solution was shaken with 1 ml saturated sodium chloride solution and dried over anhydrous sodium sulfate. The ether was evaporated with a nitrogen stream and the residue dissolved in 1 ml of 0.1 N hydrochloric acid which was treated with 0.6 ml of 0.1 N sodium hydroxide to obtain a final pH of 4.5. Radiochemical purity by radiochromatography was 100%.

Other compounds prepared in the preceeding examples were labeled by this procedure as noted in table I in example 21.

EXAMPLE 16

In accordance with the procedure of example 15, N-methyl-o-iodo-β-phenylamine prepared in example 6 and p-iodoaniline were labeled with the addition of 40 mcg iodine monochloride to the reaction mixture.

EXAMPLE 17

In accordance with the procedure of example 15, N-β-phenyl-p-iodoaniline and N,N-dibenzyl-p-iodoaniline prepared in example 5 were labeled with the addition of 50 mcg of copper nitrate to the reaction mixture.

EXAMPLE 18

Ten mg of N-isopropyl-m-iodobenzylamine hydrochloride prepared in example 3 was dissolved in 0.1 ml methanol, treated with 0.1 ml of 10 N sodium hydroxide and extracted with 1 ml ether. The ether solution was separated, washed with 1 ml water, 1 ml saturated sodium chloride solution, dried over anhydrous magnesium sulfate and centrifuged. Approximately 0.7 ml of the supernatant was transferred to a tared 8 mm pyrex test tube, and the ether evaporated in a stream of nitrogen. The product was then labeled in accordance with the procedure of example 15.

Additional compounds labeled by this procedure are indicated in table I.

EXAMPLE 19

N-o-Iodobenzylamine was labeled according to the procedure of example 15 through washing with potassium iodide, sodium bisulfite and water. After these washings, the ether solution was dried by shaking with two 1 ml portions of saturated sodium chloride solution followed by anhydrous sodium sulfate. The solvent was evaporated in a nitrogen stream. The residue was taken up in 50 mcl of ether and applied in a row of 5 spots to a plate (4 cm × 10 cm) of silica gel 60-F and the plate developed with 50% $CHCl_3$/hexane. The uv-absorbing band at $R_f$ 0.6–0.7 corresponding to the desired product was cut from the strip and eluted with three 1 ml portions of ether. The eluate was evaporated with a nitrogen stream and the residue taken up in 1.1 ml ethanol followed by 1.1 ml water. Radiochemical purity by TLC 50% $CHCl_3$/hexane, $R_f$=0.67, was 100%.

Other compounds labeled by this procedure are indicated in table I.

EXAMPLE 20

A solution of 1 mg of I-123-o-iodobenzaldehyde prepared in accordance with example 15 in 100 mcl ethanol was placed in a small test tube. One lambda of aniline was added and the mixture allowed to stand for ten minutes. A solution of 2 mg of sodium cyanide in 10 lambda of deionized water was then added and the mixture allowed to stand for an additional ten minutes. Three lambda of acetic acid was then added and the mixture allowed to stand 20 minutes to yield α-anilino-o-iodophenylacetonitrile.

EXAMPLE 21

Bioassays were performed utilizing compounds from the foregoing examples labeled with I-123 in accordance with the method described in examples 15–20. Female Sprague-Dawley rats weighing approximately 150 g were anesthetized with sodium pentobarbital and were injected in a tail vein with from 0.05 to 1.0 mCi (in a volume of 0.2 to 0.5 ml) of the I-123-labeled compound. Two specimens were utilized for each test.

Two animals each were sacrificed at 5 minutes and 60 minutes post-injection, the tails discarded and the amount of activity in various organs determined. Each organ was counted at a standardized geometry with a sodium iodide crystal scintillation counter adjusted for the 159 keV emission of I-123. The organs were also weighed to one thousandth of a gram and the activity calculated as a percent of administered dose per gram of organ weight.

The ratio of brain-to-blood activity was calculated as a percent of administered dose per gram. The results for blood, brain and heart as well as the brain/blood ratio are reported in table I. For comparative purposes, I-123 antipyrine was utilized as a standard.

TABLE I

| Compound | Labeled by Example No. | Percent Dose/Gram | | | | | | Brain/Blood Ratio | |
| --- | --- | --- | --- | --- | --- | --- | --- | --- | --- |
| | | Blood | | Brain | | Heart | | | |
| | | 5 min. | 60 min. | 5 min. | 60 min. | 5 min. | 60 min. | 5 min. | 60 min. |
| I—123-o-iodoaniline | 19 | 1.70 | 0.44 | 0.47 | 0.03 | 1.02 | 0.17 | 0.28 | 0.07 |
| I—123-p-iodoaniline | 16 | 0.97 | 0.80 | 1.09 | 0.80 | 1.11 | 0.80 | 1.12 | 1.00 |
| I—123-N—benzyl-o-iodoaniline | 19 | 0.30 | 0.36 | 0.67 | 0.29 | 0.34 | 1.25 | 2.23 | 0.80 |
| I—123-N—β-phenethyl-o-iodoaniline | 19 | 1.04 | 0.48 | 1.29 | 0.16 | 1.16 | 0.33 | 1.24 | 0.33 |
| I—123-N—isopropyl-o-iodoaniline | 19 | 0.78 | 0.50 | 0.88 | 0.13 | 0.75 | 0.29 | 1.13 | 0.26 |
| I—123-N—benzyl-p-iodoaniline | 15 | 1.00 | 0.86 | 1.57 | 0.44 | 1.28 | 0.59 | 1.57 | 0.51 |
| I—123-N—β-phenethyl-p-iodoaniline | 17 | 0.88 | — | 0.93 | — | 1.38 | — | 1.06 | — |
| I—123-N—isopropyl-p-iodoaniline | 19 | 0.48 | 0.79 | 1.23 | 0.26 | 1.01 | 0.61 | 2.55 | 0.33 |
| I—123-N—(o-iodophenyl) amphetamine (dl) | 19 | 0.53 | 0.55 | 0.96 | 0.41 | 1.64 | 0.57 | 1.81 | 0.75 |

TABLE I-continued

| Compound | Labeled by Example No. | Percent Dose/Gram | | | | | | Brain/Blood Ratio | |
|---|---|---|---|---|---|---|---|---|---|
| | | Blood | | Brain | | Heart | | | |
| | | 5 min. | 60 min. | 5 min. | 60 min. | 5 min. | 60 min. | 5 min. | 60 min. |
| I—123-α-(p-iodoanilino)phenylacetamide | 15 | 0.71 | — | 0.92 | — | 1.42 | — | 1.30 | — |
| I—123-N,N—dibenzyl-p-iodoaniline | 17 | 0.66 | 0.41 | 0.35 | 0.22 | 2.10 | 0.46 | 0.53 | 0.54 |
| I—123-N—ethyl-o-iodobenzylamine | 19 | 0.25 | 0.34 | 1.06 | 0.44 | 0.79 | 0.44 | 4.22 | 1.31 |
| I—123-N—propyl-o-iodobenzylamine | 19 | 0.27 | 0.32 | 1.03 | 0.59 | 0.77 | 0.59 | 3.81 | 1.84 |
| I—123-N—β-phenethyl-o-iodobenzylamine | 18 | 0.27 | 0.14 | 0.68 | 0.14 | 0.56 | 0.15 | 2.52 | 0.96 |
| I—123-N—isopropyl-o-iodobenzylamine | 18 | 0.16 | 0.62 | 1.21 | 0.64 | 0.72 | 0.47 | 7.63 | 1.04 |
| I—123-N—t-butyl-o-iodobenzylamine | 15 | 0.17 | 0.11 | 1.49 | 0.89 | 1.04 | 0.49 | 8.85 | 8.16 |
| I—123-N—o-iodobenzylaniline | 15 | 0.61 | 0.41 | 1.02 | 0.17 | 0.83 | 0.31 | 1.70 | 0.41 |
| I—123-N—o-iodobenzylamphetamine (dl) | 19 | 0.27 | 0.19 | 1.06 | 0.36 | 0.72 | 0.37 | 3.93 | 1.89 |
| I—123-N—isopropyl-m-iodobenzylamine | 18 | 0.22 | 0.21 | 1.61 | 0.85 | 0.99 | 0.46 | 7.35 | 4.16 |
| I—123-N,N—di-β-phenethyl-o-iodobenzylamine | 15 | 1.03 | — | 1.06 | — | 3.61 | — | 1.03 | — |
| I—123-N,N—di-o-iodobenzylethylamine | 19 | 0.52 | 0.28 | 0.36 | 0.25 | 2.11 | 0.50 | 0.68 | 0.88 |
| I—123-N,N—diisopropyl-o-iodobenzylamine | 18 | 0.25 | 0.35 | 1.40 | 0.46 | 2.12 | 0.46 | 5.73 | 1.31 |
| I—123-N—o-iodobenzylpiperidine | 18 | 0.60 | 0.32 | 0.93 | 0.29 | 0.56 | 0.38 | 1.56 | 0.91 |
| I—123-N—o-iodobenzyl-2,6-dimethylpiperidine | 15 | 0.31 | 0.21 | 1.01 | 0.32 | 1.14 | 0.44 | 3.32 | 1.59 |
| I—123-N—o-iodobenzyl-2,5-dimethylpyrrolidine | 15 | 0.37 | 0.15 | 1.16 | 0.22 | 1.03 | 0.46 | 3.17 | 1.52 |
| I—123-α-amino-o-iodophenylacetonitrile | 15 | 0.34 | — | 0.58 | — | 0.86 | — | 1.74 | — |
| I—123-α-anilino-o-iodophenylacetonitrile | 20 | 0.17 | 0.10 | 0.80 | 0.14 | 0.90 | 0.24 | 4.68 | 1.41 |
| I—123-o-iodo-β-phenethylamine | 15 | 1.43 | — | 0.70 | — | 1.22 | — | 0.49 | — |
| I—123-N—methyl-o-iodo-β-phenethylamine | 16 | 1.16 | — | 0.57 | — | 1.07 | — | 0.49 | — |
| I—123-N—propyl-o-iodo-β-phenethylamine | 18 | 0.29 | 0.20 | 1.17 | 0.44 | 1.54 | 0.23 | 4.03 | 2.20 |
| I—123-N—isopropyl-o-iodo-β-phenethylamine | 19 | 0.12 | 0.12 | 1.03 | 0.67 | 0.88 | 0.27 | 8.58 | 5.83 |
| I—123-N—β-phenethyl-o-iodo-β-phenethylamine | 19 | 0.16 | 0.09 | 0.74 | 0.48 | 1.56 | 0.26 | 4.77 | 5.17 |
| I—123-N—o-iodo-β-phenethylamphetamine (dl) | 19 | 0.12 | 0.11 | 0.82 | 0.83 | 2.02 | 0.48 | 7.13 | 7.86 |
| I—123-N—(2,6-dimethylphenylcarbamoyl)methyl-o-iodo-β-phenethylamine | 19 | 0.55 | 0.26 | 0.73 | 0.08 | 0.74 | 0.21 | 1.33 | 0.31 |
| I—123-N—o-iodo-β-phenethylpiperidine | 19 | 0.46 | — | 1.08 | — | 1.68 | — | 2.35 | — |
| I—123-N,N—di-β-phenethyl-o-iodo-β-phenethylamine | 19 | 0.83 | 0.65 | 0.20 | 0.11 | 1.18 | 0.62 | 0.24 | 0.17 |
| I—123-N—β-phenethyl-N—isopropyl-o-iodo-β-phenethylamine | 15 | 0.29 | — | 0.53 | — | 2.01 | — | 1.83 | — |
| I—123-R—p-iodoamphetamine | 15 | 0.15 | 0.12 | 1.38 | 2.07 | 2.43 | 1.09 | 10.60 | 18.50 |
| I—123-S—p-iodoamphetamine | 15 | 0.17 | 0.17 | 1.22 | 1.88 | 1.52 | 0.86 | 7.04 | 11.30 |
| I—123-R—N—isopropyl-p-iodoamphetamine | 15 | 0.14 | 0.11 | 1.57 | 2.14 | 1.78 | 0.87 | 12.60 | 20.70 |
| I—123-S—N—isopropyl-p-iodoamphetamine | 15 | 0.11 | 0.13 | 1.32 | 1.93 | 1.28 | 0.85 | 12.80 | 15.40 |
| I—123-iodoantipyrine[a] | — | 1.26 | 0.94 | 0.61 | 0.17 | 0.98 | 0.53 | 0.48 | 0.18 |

[a]Prepared according to J. Nucl. Med., 17, 1093 (1976).

We claim:
1. A radioiodinated amine of the formula:

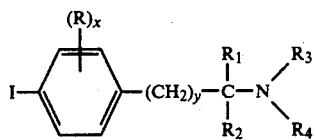

wherein I is a radioisotope of iodine, R is lower alkyl or halogen; $R_1$ is hydrogen or lower alkyl; $R_2$ is lower alkyl; $R_3$ and $R_4$ are the same or different and are selected from the group consisting of hydrogen, alkyl, aryl, substituted aryl, aralkyl, substituted aralkyl and carbamoylmethyl or $R_3$ and $R_4$ taken together with the nitrogen to which they are attached form a 5- or 6-membered ring which may be substituted with one or more lower alkyl groups, and x is 0 to 4 and y is 0 to 3.

2. The compound of claim 1 wherein said compound is I-123-p-iodo-alpha-methylbenzylamine.

3. The compound of claim 1 wherein said compound is I-123-N-isopropyl-p-iodo-alpha-methylbenzylamine.

4. The compound of claim 1 wherein said compound I-123-R-p-iodoamphetamine.

5. The compound of claim 1 wherein said compound is I-123-S-p-iodoamphetamine.

6. The compound of claim 1 wherein said compound is I-123-R-N-isopropyl-p-iodoamphetamine.

7. The compound of claim 1 wherein said compound is I-123-S-N-isopropyl-p-iodoamphetamine.

8. A method of imaging the brain comprising intraveneously injecting an effective amount of a composition comprising a compound of claim 1 in a carrier suitable for intravenous injection and scanning the brain with scintiscanning means.

9. A method in accordance with claim 8 wherein said compound is I-123-p-iodo-α-methylbenzylamine.

10. A method in accordance with claim 8 wherein said compound is I-123-N-isopropyl-p-iodo-α-methylbenzylamine.

11. A method in accordance with claim 8 wherein said compound is I-123-R-p-iodoamphetamine.

12. A method in accordance with claim 8 wherein said compound is I-123-S-p-iodoamphetamine.

13. A method in accordance with claim 8 wherein said compound is I-123-R-N-isopropyl-p-iodoamphetamine.

14. A method in accordance with claim 8 wherein said compound is I-123-S-N-isopropyl-p-iodoamphetamine.

* * * * *

UNITED STATES PATENT AND TRADEMARK OFFICE

CERTIFICATE EXTENDING PATENT TERM
UNDER 35 U.S.C. 156

Patent No.    : 4,360,511

Dated         : November 23, 1982

Inventor(s)   : Ronald M. Baldwin et al

Patent Owner  : Medi-Physics, Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Twenty-Eighth day of December 1988.

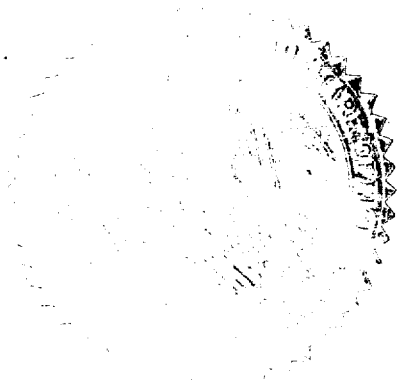

Donald J. Quigg

Assistant Secretary and Commissioner of Patents and Trademarks